United States Patent
Lee et al.

(10) Patent No.: US 10,085,942 B2
(45) Date of Patent: Oct. 2, 2018

(54) NANOPARTICLES, METHOD OF PREPARING THE SAME AND THEIR USE

(71) Applicant: City University of Hong Kong, Kowloon (HK)

(72) Inventors: Chun-Sing Lee, Kowloon (HK); Xiaohong Zhang, Suzhou (CN); Jinfeng Zhang, Kowloon Tong (HK); Fu-Lung Wong, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 14/945,723

(22) Filed: Nov. 19, 2015

(65) Prior Publication Data

US 2017/0143633 A1    May 25, 2017

(51) Int. Cl.
| | | |
|---|---|---|
| *A61K 9/19* | (2006.01) | |
| *A61K 31/12* | (2006.01) | |
| *A61K 31/337* | (2006.01) | |
| *A61K 31/444* | (2006.01) | |
| *A61K 31/4745* | (2006.01) | |
| *A61K 9/14* | (2006.01) | |
| *A61K 9/16* | (2006.01) | |

(52) U.S. Cl.
CPC ............... *A61K 9/19* (2013.01); *A61K 9/14* (2013.01); *A61K 31/12* (2013.01); *A61K 31/337* (2013.01); *A61K 31/444* (2013.01); *A61K 31/4745* (2013.01); *A61K 9/1688* (2013.01)

(58) Field of Classification Search
CPC ....................................................... A61K 9/19
See application file for complete search history.

(56) References Cited

U.S. PATENT DOCUMENTS

| 8,304,758 B2 | 11/2012 | Fang |
| 8,558,019 B2 | 10/2013 | Kingston |
| 8,785,371 B2 | 7/2014 | Patil |
| 8,889,188 B2 | 11/2014 | Fang |

FOREIGN PATENT DOCUMENTS

CN         103191019     *  7/2013

\* cited by examiner

*Primary Examiner* — Brian E McDowell
(74) *Attorney, Agent, or Firm* — Renner Kenner Greive Bobak Taylor & Weber

(57) ABSTRACT

The present invention provides nanoparticles and a method of preparing the nanoparticles by using an ice template. Pharmaceutical formulations including such nanoparticles and their use are also described. The method allows for an environmentally friendly provision of advantageously small particles with higher production rate and improved reproducibility.

8 Claims, 5 Drawing Sheets

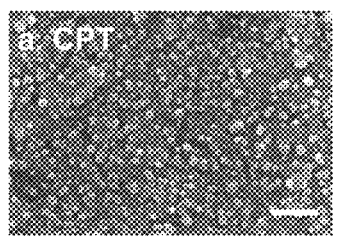
Fig. 3A  Fig. 3B  Fig. 3C
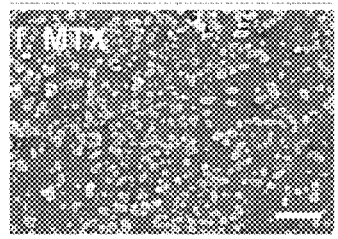
Fig. 3D  Fig. 3E  Fig. 3F
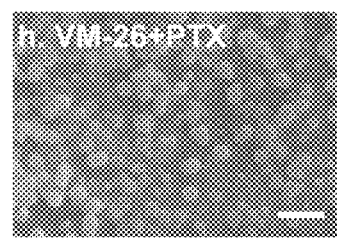
Fig. 3G  Fig. 3H  Fig. 3I

NANOPARTICLES, METHOD OF PREPARING THE SAME AND THEIR USE

TECHNICAL FIELD

The present invention relates to a method of preparing nanoparticles by using an ice template and the nanoparticles obtained from said method. The invention further refers to a pharmaceutical formulation comprising said nanoparticles as well as its use.

BACKGROUND

Conventional methods for preparing pure nanodrugs (PNDs) include re-precipitation which is also called solvent-exchange process. The solvent-exchange process is generally based on the relative solubility of the drug compound in two immiscible liquids such as water and an organic solvent. When the organic solvent containing the drug compounds comes into the contact with the non-solvent such as water, the drug compound will be precipitated to form particles. However, there are several drawbacks associated with such processes, for example, large batch-to-batch variations, low production rates and relatively large particle sizes.

Recently, a method for preparing size controllable nano-drugs (NDs) has been described representing an anodized aluminum oxide (AAO) template-assisted method. Although this AAO template-assisted approach allows the production of nanoparticles with improved reproducibility and allows for a higher production rate, the use of the organic template is associated with several problems such as contamination and biodegradation of the possible trace amount of aluminum residues.

Accordingly, there remains a strong need for developing an environmentally friendly and effective process to prepare nanoparticles of compounds, especially drug compounds, with small particle size, high production rate and high reproducibility. Especially when preparing nanoparticles of drug compounds, it is very important to ensure a sufficient purity while avoiding traces of compounds which could negatively impact health.

SUMMARY OF THE INVENTION

The present invention refers in an aspect to a method of preparing nanoparticles of a compound by using an ice template, comprising an application step in which a solution containing the compound and a solvent is applied to the ice template. Said method further comprises a solvent removing step in which said solvent is removed from the ice template.

In a further aspect, the invention refers to nanoparticles obtained from said method.

Still further, the present invention provides a pharmaceutical composition comprising the nanoparticles obtained from said method.

The method according to the invention allows for an environmentally friendly provision of advantageously small particles with higher production rate and improved reproducibility compared to known methods. The nanoparticles obtained from the method of the present invention have an advantageously higher water dispersibility and bioavailability when compared with the compound in free form. The nanoparticles also exhibit improved cell penetration efficiency over the compound in free from. Accordingly, the nanoparticles can further achieve a promising efficacy when applied in a pharmaceutical composition for treating or preventing a disease with reduced side effects which may be, for example, caused by the presence of organic solvents.

BRIEF DESCRIPTION OF THE DRAWINGS

FIG. 3A is a SEM image of camptothecin (CPT) nanoparticles prepared by using the ice template (scale bar 500 nm).

FIG. 3B is a SEM image of paclitaxel (PTX) nanoparticles prepared by using the ice template (scale bar 500 nm).

FIG. 3C is a SEM image of mercaptopurine (6-MP) nanoparticles prepared by using the ice template (scale bar 500 nm).

FIG. 3D is a SEM image of squaric acid (SQ) nanoparticles prepared by using the ice template (scale bar 500 nm).

FIG. 3E is a SEM image of 5,10,15,20-tetra (4-pyridyl) porphyrin ($H_2$TPyP) nanoparticles prepared by using the ice template (scale bar 500 nm).

FIG. 3F is a SEM image of methotrexate (MTX) nanoparticles prepared by using the ice template (scale bar 500 nm).

FIG. 3G is a SEM image of teniposide (VM-26) nanoparticles prepared by using the ice template (scale bar 500 nm).

FIG. 3H is a SEM image of VM-26 nanoparticles together with PTX nanoparticles prepared by using the ice template (scale bar 500 nm).

FIG. 3I is a SEM image of VM-26 nanoparticles together with $H_2$TPyP nanoparticles prepared by using the ice template (scale bar 500 nm).

DETAILED DESCRIPTION OF THE INVENTION

Figure 1:
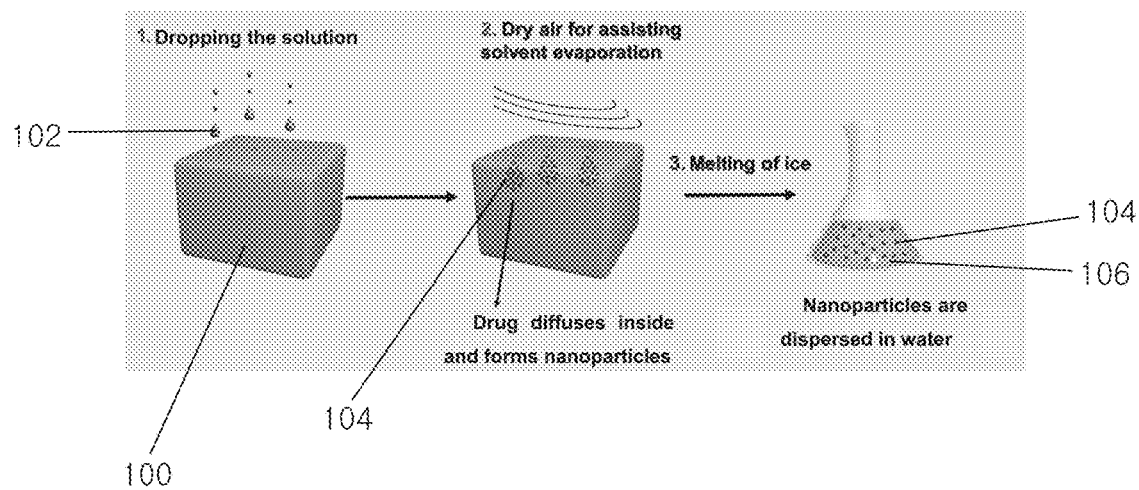
FIG. 1 is a schematic diagram showing the procedures of preparing nanoparticles by using an ice template in accordance with one embodiment of the present invention.

The present invention refers in a first aspect to a method of preparing nanoparticles of a compound by using an ice template. Said method comprises an application step in which a solution containing the compound and a solvent is applied to the ice template and a solvent removing step in which said solvent is removed from the ice template.

The term "nanoparticles" is known to the skilled person and refers to particles having an average diameter of less than 1000 nm. More preferably, the average diameter of the nanoparticles according to the invention is less than 500 nm. Further preferably, the average diameter of the nanoparticles according to the invention is less than 100 nm.

The skilled person is aware of suitable methods for determining the average diameter of particles. Preferably, the term "nanoparticles" refers to particles having an average diameter of less than 1000 nm as determined by dynamic light scattering. More preferably, the nanoparticles of the present invention have an average diameter of less than 500 nm as measured by dynamic light scattering, still more preferably of less than 100 nm as measured by dynamic light scattering.

The term "ice template" of the present invention refers to a frozen material present in solid form. The ice template may be of any appropriate size or dimension and is suitable to provide at least one surface for a solution containing the compound and a solvent to apply said solution onto or into said ice template.

Preferably, the ice template of the present invention comprises frozen water and in particular frozen deionized water. More preferably, the ice template consists of frozen water, in particular frozen deionized water, which more preferably excludes any relevant and undesired impurities in the ice template. In particular, the ice template is prepared by freezing a solution comprising and more preferably consisting of water preferably deionized water preferably at a temperature lower than 0° C., preferably at a temperature of around −250° C. to around 0° C., in particular by freezing said solution in −20° C. refrigerator or by freezing said solution in liquid nitrogen. Hence, said method of the invention preferably further comprises a preparation step before the application step in which the ice template is prepared from a solution comprising water by freezing.

Preferably, the compound of the present invention is a hydrophobic compound. The term "hydrophobic compound" is known to a skilled person. It generally refers to a compound being not soluble in water or having poor water solubility. "Hydrophobic compound" preferably refers to a compound having a water-solubility of less than 10 g/L and further preferably of less than 1 g/L in water at 20° C. In some preferred embodiments, the water-solubility of the hydrophobic compound is even less than 0.1 g/L in water at 20° C.

In preferred embodiments, the hydrophobic compound can be a pharmaceutically active compound, i.e. a drug compound used or suitable for therapeutically treating or preventing a disease. For example, the pharmaceutically active compound may be a compound suitable to treat or prevent autoimmune diseases, cancers, cardiovascular diseases, gastrointestinal diseases, diabetes, inflammatory diseases etc. In particular, the compound can be an active pharmaceutical compound, preferably a chemotherapeutic agent. Preferably, the active pharmaceutical compound is selected from the group consisting of curcumin, camptothecin, paclitaxel, 6-mercaptopurine, squaric acid, methotrexate, teniposide, carmustine, tamoxifen, etoposide, fluorouracil and a combination thereof or other hydrophobic chemotherapeutics. More preferably, the active pharmaceutical compound is a chemotherapeutic agent selected from the group consisting of curcumin, camptothecin, paclitaxel, 6-mercaptopurine, squaric acid, methotrexate, teniposide, carmustine, tamoxifen, etoposide, fluorouracil and a mixture thereof. Other known hydrophobic active compounds, especially chemotherapeutic agents, as well as their derivatives, may also be applied in the present invention.

In other embodiments, the hydrophobic compound can be a photosensitizer that sensitizes an organism, cell, or tissue to light, the photosensitizer may be an agent applied in photodynamic therapy. Preferably, the photosensitizer is selected from the group consisting of 5,10,15,20-tetra(4-pyridyl)porphyrin, zinc phthalocyanine, chlorin e6, protoporphyrin IX, tetraphenylporphyrin, 5,10,15,20-tetra-(m-hydroxyphenyl)chlorin and a derivative of one of these compounds or other hydrophobic photosensitizers. In preferred embodiments, the photosensitizer can be 5, 10, 15, 20-tetra(4-pyridyl)porphyrin, zinc phthalocyanine or a derivative of one of these compounds. The skilled person will also appreciate that other hydrophobic photosensitizers that are commonly used, as well as their derivatives, may be applied in the present invention.

The method of the present invention is advantageous in that it allows for a provision of the pharmaceutical compound in a nano-scale with high dispersity and eliminates the risk of a contamination with undesired solvent residues in the nanoparticles obtained.

With reference to FIG. 1, in one embodiment, the method of preparing nanoparticles of a compound by using an ice template includes an application step (1) in which a solution containing the compound and a solvent is applied to the ice template, a solvent removing step (2) in which the solvent is removed from the ice template, and a releasing step (3) in which the nanoparticles are released from the ice template.

In this preferred embodiment, the ice template 100 is an ice cube consisting of and made of deionized frozen water, and the solution 102 applied consists of a drug compound dissolved in a solvent such as ethanol. Specifically, the solution 102 is applied to the surface of the ice template 100 by dropping. Alternatively, other possible ways for delivering the solution to the ice template may be applied, such as using a nozzle to spray the solution to the ice template, and using a syringe to inject the solution to the ice template.

In the application step of the method of the present invention, the solution is preferably applied to the ice template by dropping, injection or spraying Preferably, the solvent in the method of the present invention is an organic solvent. The organic solvent may be selected from the group consisting of an alcohol, an ether, an ester, a halogenated alkane, a cycloalkane and a mixture thereof. More preferably, the organic solvent is an alcohol which is preferably volatilizable. The alcohol may be ethanol, methanol, propanol, butanol or a mixture thereof. In other embodiments, the organic solvent may be tretrahydrofuran (THF), acetone, dichloromethane, chloroform etc.

The solution containing the compound and the solvent is preferably applied to the ice template at least one time. More preferably, the solution is applied to the ice template two or more than two times which depends on the desired yield, the volume of the solution applied and the concentration of the compound in the solution. In one embodiment, the solution is applied to the ice template with a volume of about 5-5000 µL at least one time. The skilled person will understand that the volume applied may vary according to the selected conditions of the process. In a preferred embodiment, the solution preferably contains around 0.1-50 mg/mL of the compound as such this low concentration will allow the nanoparticles to be formed even in a smaller size.

After applying the solution to the ice template in the application step (1), the solvent is removed from the ice template in a solvent removing step. The solvent is removed from the ice template preferably by natural evaporation or by blowing with air, nitrogen gas or argon gas such as shown in FIG. 1. "Natural evaporation" preferably refers to an evaporation process conducted under an air environment without using additional evaporating means, i.e. means usually applied to remove a solvent, such as varying the temperature or pressure. For example, the solvent is removed by exposing the ice template to the air without changing the environmental conditions. The solvent is then evaporated naturally. In alternative embodiments, the solvent is removed by blowing with air, nitrogen gas or argon gas which is preferably inert and does not react with the compound. In preferred embodiments, the solvent is ethanol which is volatilizable and can be easily evaporated preferably by using gases such as ordinary air, nitrogen gas and argon gas. In particular, said gases may be used with a temperature of about 0-30° C. The removal of the solvent allows the compound to form solid nanoparticles as 104 in FIG. 1 and diffuse inside the ice template.

The method of the invention preferably further comprises a releasing step after the solvent removing step in which the nanoparticles are released from the ice template, more preferably by melting the ice template to form a dispersion comprising the nanoparticles. Hence, in the releasing step, the ice template is preferably melted to release the nanoparticles from the ice template. With reference to FIG. 1, the ice template 100 is melted to form a dispersion such as 106 comprising the nanoparticles 104. Optionally, the dispersion may undergo ultrasonication for a period of at least 1 min, and preferably about 5-60 min, to ensure that the nanoparticles are well-distributed in the dispersion which could be desirable depending on the application of the nanoparticles such as preparation of a pharmaceutical composition for treating or preventing a disease or a condition.

Alternatively, the nanoparticles are released in the releasing step from the ice template by evaporating the ice template. For example, the ice template may be placed in a dry oven for evaporation of material of the ice template.

In some preferred embodiments, a further freezing step may be applied between the solvent removing step and the releasing step. In said preferred freezing step, the ice template is frozen preferably by storing the ice template under 0° C., preferably at a temperature of around −250° C. to around 0° C., in particular by storing the ice template in −20° C. refrigerator for a period of at least 0.5 h or by using liquid nitrogen. More preferably, the ice template may be stored in said refrigerator for at least 1 h and further preferably about 1-48 h. In an advanced embodiment, the ice template may be frozen by using the liquid nitrogen first before storing in the refrigerator. It may be advantageous to additionally apply said freezing step as it allows for an additional aging process suitable to further stabilize the nanoparticles formed on or in the ice template. Furthermore, if there are more than one application steps, as well as solvent removing steps, the freezing step may be performed after each time the solvent is removed from the ice template.

The method according to the invention allows for an easily applicable, cost efficacious and environmentally friendly provision of advantageously small particles with higher production rate, exceptional yield and improved reproducibility compared to known methods. Said method is especially suitable for producing nanoparticles of hydrophobic drugs. The present invention, hence, illustrates an environmental friendly method for preparing nanoparticles of a hydrophobic compound in a milder preparation environment. Such method also saves a lot of efforts in deriving a custom molecular modification for the hydrophobic molecules in the preparation of the nanoparticles.

Figure 4A:
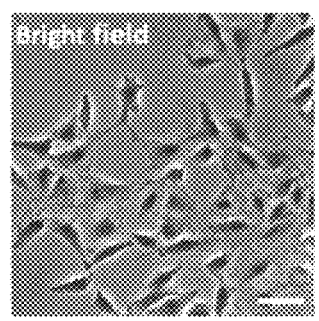
FIG. 4A is an in vitro cell imaging of A549 cells under bright field after treating the cells with CUR nanoparticles.
Figure 4B:
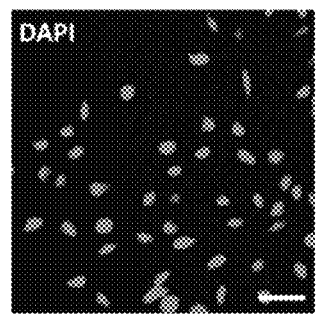
FIG. 4B is a fluorescent image of A549 cells having nucleus stained with 4',6-diamidino-2-phenylindole (DAPI) after the treatment with CUR nanoparticles.
Figure 4C:
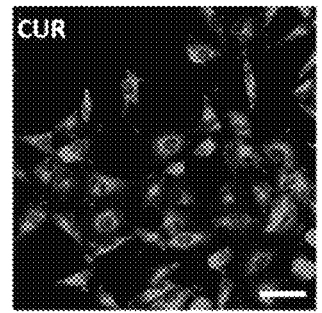
FIG. 4C is a fluorescent image of A549 cells with CUR being stained after the treatment with CUR nanoparticles.
Figure 4D:
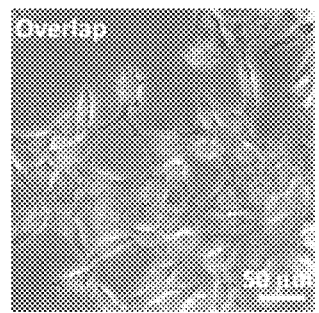
FIG. 4D is a combined image of FIGS. 4A to 4C.
Figure 5:
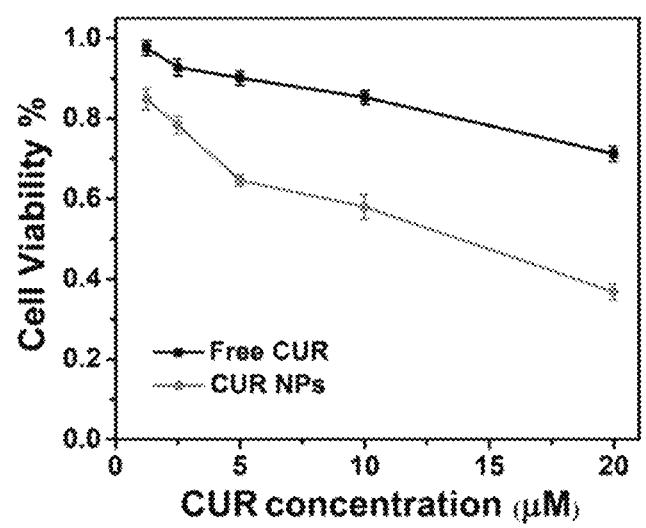
FIG. 5 shows the relative cell viability of A549 cells after treatment with different concentrations of free CUR and CUR nanoparticles, namely 1.25 µM, 2.5 µM, 5 µM, 10 µM and 20 µM for 48 hours.

The nanoparticles obtained from the method described above show exceptional water dispersibility and bioavailability, as well as good cellular uptake ability which has been observed by confocal microscopy as shown in FIG. 4A-4D. As depicted in FIG. 4C, a strong cytoplasmic green fluorescence surrounding nuclei within the A549 cells is clearly observed, indicating accumulation of CUR PNDs and subsequently release of CUR molecules in cells. In addition, the nanoparticles also exhibit better therapeutic efficacy against some diseases and conditions such as cancer and exhibit fewer side effects, as shown in FIG. 5 on testing the cell viability of the curcumin nanoparticles obtained from the method of the present invention by MTT assay. MTT assay is a colorimetric assay for assessing cell metabolic activity which reflects the number of viable cells present under defined conditions. The increase in efficacy is due to the higher drug loading capacity of the nanoparticles of the present invention when compared with the ordinary carried based one, which leads to an improvement in drug delivery system. The nanoparticles obtained from the method of the present invention can be applied in various applications in medical and research fields. The removal of the organic solvent substantially reduces side effects that may have in the for example native drug molecules.

Figure 2A:
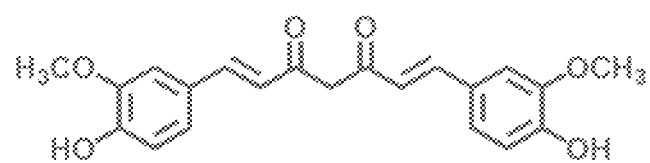
FIG. 2A shows the chemical structure of curcumin (CUR).
Figure 2B:
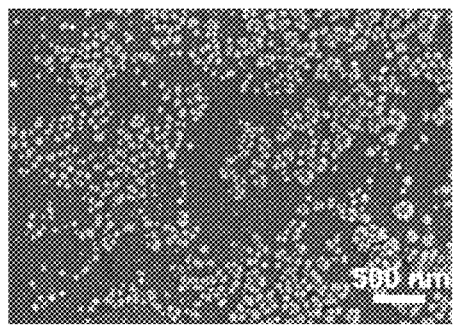
FIG. 2B shows a scanning electron micrograph (SEM) of CUR nanoparticles obtained by using the ice template (scale bar 500 nm).
Figure 2C:
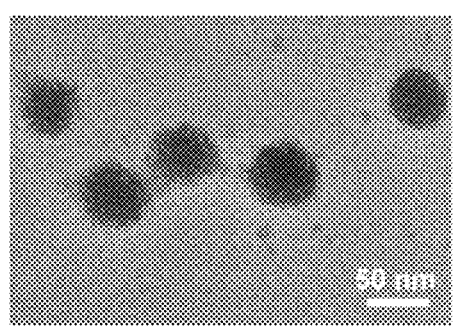
FIG. 2C shows a transmission electron microscopy (TEM) image of CUR nanoparticles obtained by using the ice template, wherein the nanoparticles appear as uniform spherical particles.
Figure 2D:
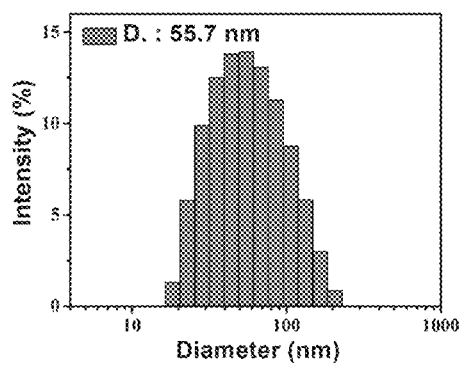
FIG. 2D shows a dynamic light scattering measurement of CUR nanoparticles, the CUR nanoparticles in deionized water have an average diameter of 55.7 nm.
Figure 2E:
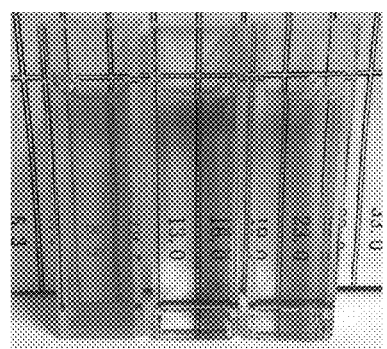
FIG. 2E is a photograph showing aqueous dispersions of free CUR powder (d1), CUR nanoparticles prepared by using the ice template (d2), and CUR nanoparticles prepared by conventional re-precipitation method (d3).

Further in accordance with the invention are nanoparticles obtained according to the method of the invention, preferably nanoparticles having an average diameter of less than 500 nm, more preferably of less than 100 nm, preferably measured in an aqueous solution using a dynamic light scattering (DLS) instrument (Malvern Nano Zetasizer). DLS can be used to determine the size distribution profile of small particles in solution by measuring fluctuations in scattered light intensity made by diffusing particles, as shown in FIG. 2D.

Furthermore, the present invention refers to a pharmaceutical composition comprising said nanoparticles of a compound preferably in addition to pharmaceutically tolerable excipients, wherein the compound is a drug compound. The skilled person is able to select appropriate excipients. The drug compound is preferably a hydrophobic compound, still more preferably an active pharmaceutical compound selected from the group consisting of curcumin, camptothecin, paclitaxel, 6-mercaptopurine, squaric acid, methotrexate, teniposide and a mixture thereof.

The examples set out below further illustrate the invention. The preferred embodiments described above and the drawing as well as examples given below represent preferred or exemplary embodiments and a skilled person will understand that the reference to those embodiments or examples is not intended to be limiting.

Example 1

Preparation of Curcumin Nanoparticles

Curcumin (CUR) is a kind of hydrophobic compound used as a chemotherapeutic agent in treating diseases like cancer, gastrointestinal diseases and cognitive disorders. The nanoparticles of CUR, as shown in FIGS. 2B and 2C, were prepared as follows.

Firstly, the ice templates were prepared by directly freezing deionized water in −20° C. refrigerator. Secondly, CUR was dissolved in acetone to form a solution having a concentration of 6 mg/mL of CUR, then 300 μL of the solution were injected to the ice template by a syringe. Thirdly, acetone was volatilized and removed with the assistance of 25° C. air-blowing, as such CUR nanoparticles were gradually formed in the tiny gaps and cracks between the ice matrixes. During the above-mentioned steps, the ice template was placed on an ice pedestal so as to prevent the ice template from melting.

Subsequently, the ice templates treated with the solution were stored in −20° C. refrigerator for 12 hours in order to further age the formation process. Finally, the ice template was removed by directly melting and the CUR nanoparticles were released in a dispersion. The dispersion was further ultrasonicated for 10 min.

Example 2

Preparation of Camptothecin Nanoparticles

Camptothecin (CPT) is a kind of hydrophobic compound used as a chemotherapeutic agent in treating or preventing cancer. The nanoparticles of CPT, as shown in FIG. 3A, were prepared as follows.

Firstly, the ice templates were prepared by freezing deionized water in the liquid nitrogen. Secondly, CPT was dissolved in ethanol to form a solution having a concentration of 1 mg/mL of CPT, then 200 µL of the solution were applied to the ice template by dropping. Thirdly, ethanol was volatilized and removed with the assistance of 25° C. nitrogen-blowing, as such CPT nanoparticles were gradually formed in the tiny gaps and cracks between the ice matrixes. During the above-mentioned steps, the ice template was placed on an ice pedestal so as to prevent the ice template from melting.

Subsequently, the ice templates treated with the solution were stored in −20° C. refrigerator for 24 hours in order to further age the formation process. Finally, the ice template was removed by directly melting and the CPT nanoparticles were released in a dispersion. The dispersion was further ultrasonicated for 15 min.

Example 3

Preparation of Paclitaxel Nanoparticles

Paclitaxel (PTX) is a kind of hydrophobic compound used as a chemotherapeutic agent in treating cancers. The nanoparticles of PTX, as shown in FIG. 3B, were prepared as follows.

Firstly, the ice templates were prepared by freezing deionized water in −20° C. refrigerator. Secondly, PTX was dissolved in tetrahydrofuran (THF) to form a solution having a concentration of 3 mg/mL of PTX, then 500 µL of the solution were injected to the ice template by using a syringe. Thirdly, THF was volatilized and removed with the assistance of 25° C. air-blowing, as such PTX nanoparticles were gradually formed in the tiny gaps and cracks between the ice matrixes. During the above-mentioned steps, the ice template was placed on an ice pedestal so as to prevent the ice template from melting.

Subsequently, the ice templates treated with the solution were stored in −20° C. refrigerator for 5 hours in order to further age the formation process. Finally, the ice template was removed by directly melting and the CPT nanoparticles were released in a dispersion. The dispersion was further ultrasonicated for 30 min.

Example 4

Preparation of 5,10,15,20-tetra(4-pyridyl)porphyrin Nanoparticles 5,10,15,20-tetra(4-pyridyl)porphyrin ($H_2TPyP$) is a kind of hydrophobic photosensitizer. The nanoparticles of $H_2TPyP$, as shown in FIG. 3E, were prepared as follows.

Firstly, the ice templates were prepared by freezing deionized water in the liquid nitrogen. Secondly, $H_2TPyP$ was dissolved in THF to form a solution having a concentration of 10 mg/mL of $H_2TPyP$, then 1000 µL of the solution were applied to the ice template by dropping. Thirdly, THF was volatilized and removed with the assistance of 37° C. air-blowing, as such $H_2TPyP$ nanoparticles were gradually formed in the tiny gaps and cracks between the ice matrixes. During the above-mentioned steps, the ice template was placed on an ice pedestal so as to prevent the ice template from melting.

Subsequently, the ice templates treated with the solution were stored in −20° C. refrigerator for 48 hours in order to further age the formation process. Finally, the ice template was removed by directly melting and the $H_2TPyP$ nanoparticles were released in a dispersion. The dispersion was further ultrasonicated for 5 min.

The invention claimed is:

1. A method of preparing nanoparticles of curcumin by using an ice template, comprising:
   an application step in which a solution containing curcumin compound and a solvent is injected to the ice template, wherein the ice template consists of frozen water;
   a solvent removing step in which the solvent is removed from the ice template; and
   a freezing step in which the ice template is frozen by using liquid nitrogen;
   wherein the nanoparticles have an average diameter of less than 100 nm.

2. The method of claim 1, further comprising a preparation step before the application step in which the ice template is prepared from a solution comprising water by freezing.

3. The method of claim 1, wherein the solvent is selected from the group consisting of an alcohol, an ether, an ester, a halogenated alkane, a cycloalkane and a mixture thereof.

4. The method of claim 1, wherein the solution is applied to the ice template in the application step with a volume of about 5-5000 µL at least one time.

5. The method of claim 1, wherein the solution contains 0.1-50 mg/mL of the curcumin compound.

6. The method of claim 1, further comprising a releasing step after the freezing step in which the nanoparticles are released from the ice template.

7. The method of claim 6, wherein the nanoparticles are released from the ice template by melting the ice template to form a dispersion comprising the nanoparticles.

8. The method of claim 7, wherein the dispersion is sonicated.

* * * * *